US009527929B2

(12) United States Patent
Francois et al.

(10) Patent No.: US 9,527,929 B2
(45) Date of Patent: Dec. 27, 2016

(54) OPTIMIZED CHITOSAN REACETYLATION

(71) Applicant: Sofradim Production, Trévoux (FR)

(72) Inventors: Sebastien Francois, Jassans-Riottier (FR); Sebastien Ladet, Caluire & Cuire (FR); Muriel Guerin, Anse (FR)

(73) Assignee: Sofradim Production, Trevoux (FR)

( * ) Notice: Subject to any disclaimer, the term of this patent is extended or adjusted under 35 U.S.C. 154(b) by 16 days.

(21) Appl. No.: 14/596,672

(22) Filed: Jan. 14, 2015

(65) Prior Publication Data
US 2015/0210780 A1 Jul. 30, 2015

(30) Foreign Application Priority Data

Jan. 30, 2014 (FR) ..................... 14 50716

(51) Int. Cl.
*C08B 37/08* (2006.01)
*C07H 1/08* (2006.01)
(52) U.S. Cl.
CPC ............... *C08B 37/003* (2013.01); *C07H 1/08* (2013.01)
(58) Field of Classification Search
None
See application file for complete search history.

(56) References Cited

U.S. PATENT DOCUMENTS

| | | | |
|---|---|---|---|
| 4,159,932 A | 7/1979 | Peniston et al. |
| 4,195,175 A | 3/1980 | Peniston et al. |
| 4,301,067 A | 11/1981 | Koshugi |
| 4,308,377 A | 12/1981 | Koshugi |
| 4,356,236 A | 10/1982 | Koshugi |
| 4,373,096 A | 2/1983 | Koshugi |
| 4,378,017 A | 3/1983 | Kosugi et al. |
| 4,401,807 A | 8/1983 | Koshugi |
| 4,879,340 A | 11/1989 | Moriguchi et al. |
| 4,996,307 A | 2/1991 | Itoi et al. |
| 5,620,706 A | 4/1997 | Dumitriu et al. |
| 5,897,821 A | 4/1999 | Kawasaki |
| 5,902,798 A | 5/1999 | Gouda et al. |
| 6,130,321 A | 10/2000 | Johnson et al. |
| 6,156,330 A | 12/2000 | Tsukada et al. |
| 6,251,959 B1 | 6/2001 | Kawahara et al. |
| 6,333,399 B1 | 12/2001 | Teslenko et al. |
| 6,444,797 B1 | 9/2002 | Son et al. |
| 6,589,999 B2 | 7/2003 | Gurny et al. |
| 6,867,287 B2 | 3/2005 | Carlucci et al. |
| 6,887,564 B2 | 5/2005 | Gagliardini et al. |
| 7,189,326 B2 | 3/2007 | Domard et al. |
| 7,544,785 B2 | 6/2009 | Cowan et al. |
| 8,153,612 B2 | 4/2012 | Ben-Shalom et al. |
| 8,236,781 B2 | 8/2012 | Laugier et al. |
| 8,318,913 B2 | 11/2012 | Bristow |
| 8,507,563 B2 | 8/2013 | Berger et al. |
| 8,703,924 B2 | 4/2014 | Andersson |
| 8,899,277 B2 | 12/2014 | Chiu et al. |
| 8,940,881 B2 | 1/2015 | Ifuku et al. |
| 8,945,609 B2 | 2/2015 | Schuetz et al. |
| 9,078,949 B2 | 7/2015 | Gislason et al. |
| 2001/0024655 A1 | 9/2001 | Schneider et al. |
| 2002/0018732 A1 | 2/2002 | Hung et al. |
| 2002/0068151 A1 | 6/2002 | Kim et al. |
| 2002/0177577 A1 | 11/2002 | Hung et al. |
| 2003/0034304 A1 | 2/2003 | Huang et al. |
| 2004/0242537 A1 | 12/2004 | Oh et al. |
| 2005/0042265 A1 | 2/2005 | Guillot et al. |
| 2005/0053663 A1 | 3/2005 | Struszczyk et al. |
| 2009/0075383 A1 | 3/2009 | Buschmann et al. |
| 2009/0197789 A1 | 8/2009 | Brooker et al. |
| 2010/0190704 A1 | 7/2010 | Shimada |
| 2013/0184356 A1 | 7/2013 | Andersson |
| 2014/0275291 A1 | 9/2014 | McGrath et al. |
| 2014/0314824 A1 | 10/2014 | Kim et al. |
| 2015/0065454 A1 | 3/2015 | Dupasquier et al. |
| 2015/0174153 A1 | 6/2015 | Nothias et al. |

FOREIGN PATENT DOCUMENTS

| | | | | |
|---|---|---|---|---|
| EP | 382210 A1 | 8/1990 | | |
| EP | 512849 A1 | 11/1992 | | |
| EP | 778286 A2 | 6/1997 | | |
| WO | 9004608 A1 | 5/1990 | | |
| WO | 9620730 A1 | 7/1996 | | |
| WO | 9703708 A1 | 2/1997 | | |
| WO | 9808877 A1 | 3/1998 | | |
| WO | 9938893 A1 | 8/1999 | | |
| WO | 03037935 A1 | 5/2003 | | |
| WO | 2005019272 A1 | 3/2005 | | |
| WO | 2007007014 A2 | 1/2007 | | |
| WO | WO 2008063503 A2 * | 5/2008 | ......... | C08B 37/0003 |
| WO | 2010061454 A1 | 6/2010 | | |
| WO | 2012080772 A1 | 6/2012 | | |
| WO | 2015032984 A1 | 3/2015 | | |
| WO | 2015092289 A1 | 6/2015 | | |

OTHER PUBLICATIONS

Taghizadeh et al., "Preparation, characterization, and swelling behavior of N-acetylated and deacetylated chitosons", www.sciencedirect.com, 8 pages.

* cited by examiner

Primary Examiner — Layla Berry

(57) ABSTRACT

The present invention relates to a method for the preparation of chitosan of a degree of acetylation $DA_f$, from chitosan β having a degree of acetylation $DA_i$ lower than $DA_f$, comprising at least one step of purification and at least one step of acetylation of said chitosan β, said purification step comprising at least one step of solubilization of said chitosan β in an acidic aqueous medium and at least one step of precipitation of said thus solubilized chitosan,
wherein said acetylation step is carried out in a solution on said solubilized chitosan before said precipitation step.

19 Claims, No Drawings

OPTIMIZED CHITOSAN REACETYLATION

CROSS-REFERENCE TO RELATED APPLICATIONS

This application claims priority of French Patent Application Serial No. 14/50716 filed Jan. 30, 2014, the disclosure of the above-identified application us hereby incorporated by reference in their entirety.

BACKGROUND

The present invention relates to a method for the preparation of chitosan having a determined degree of acetylation, in particular a degree of acetylation beyond 40% from chitosan β of lower degree of acetylation, with a good reproducibility and good precision.

Chitosan is a polysaccharide obtained from the deacetylation of chitin.

Chitin with cellulose is the most widespread natural polysaccharide on earth. Chitin is for example present in the exoskeletons of arthropods, in the endoskeletons of cephalopods as well as in the fungi.

Chitin is a biopolymer constituted of the repetition of units β(1-4)N-acetyl-2-amino-2-deoxy-D-glucose. Chitosan is obtained by extensive deacetylation of chitin. Thus, it is composed of units β(1-4)N-acetyl-2-amino-2-deoxy-D-glucose and units 2-amino-2-deoxy-D-glucose. The degree of acetylation (DA) of a chitosan is the percentage of units β(1-4)N-acetyl-2-amino-2-deoxy-D-glucose with respect to the total number of units β(1-4)N-acetyl-2-amino-2-deoxy-D-glucose and 2-amino-2-deoxy-D-glucose constituting this chitosan. Thus, from the chemical point of view, chitin and chitosan are distinguished from each other substantially by their degrees of acetylation which give them different properties: in particular, as opposed to chitin which is insoluble in the majority of known solvents, chitosan is soluble in weakly acidic aqueous solutions and may accordingly be easily treated and/or transformed. Chitosan, hence, is distinguished from chitin first by its capacity to be soluble in an aqueous medium. The degree of acetylation of chitosan may vary from 0 to around 55%.

Furthermore, chitin is mainly found under two different crystalline forms: chitin α and chitin β. Chitin α is substantially extracted from exoskeletons of arthropods such as lobster, crab, shrimp, whereas chitin β is extracted from the endoskeleton of cephalopods such as squid.

Chitin α has polysaccharide chains disposed in a antiparallel manner between planes of successive chains, thus, resulting in numerous hydrogen bonds. Such a structure gives chitin α an important stiffness and a low reactivity with respect to deacetylation. Chitin α is not soluble in the aqueous solvents and swells only very slightly in aqueous medium.

Chitin β, on the contrary, has polysaccharide chains all parallel to each other; the hydrogen bonds are less numerous therein, this gives chitin β a better reactivity and hydrophily. Chitin β, thus, has the capacity of highly swelling in water.

As seen above, due to its solubility in acidic aqueous medium, chitosan may be easily treated or transformed. Furthermore, chitosan has properties, such as biodegradability, bioresorbability, biocompatibility, non-toxicity, mechanical properties, which make it particularly interesting for medical applications. Thus, chitosan may be incorporated in medical devices as a constituent of implants, for example in the form of sponges or films for reinforcements of the abdominal wall, or even as excipient or support for controlled drug release systems. The pharmaceutical and medical sectors also focus on the coagulant, cicatrizing and controlled salting out properties of therapeutic agents of the chitosan. Chitosan also has antibacterial and antifungal properties.

The effectiveness of the chitosan in medical applications, and in particular its biodegradability, its enzymatic degradation rate or biodegradation kinetics, and its mechanical properties, including its swelling capacity in aqueous medium, are based on the one hand, to its molecular weight and, on the other hand, to its degree of acetylation. The latter must hence be able to be attained and characterized rigorously and particularly in a reproducible manner.

The extraction of chitin from exoskeletons of arthropods involves steps of protein and lipid hydrolysis, of depigmentation and of demineralization. Usually, the hydrolysis of proteins and lipids is carried out in presence of soda, the demineralization requiring the use of hydrochloric acid. As regards to endoskeletons of cephalopods, the latter being devoid of minerals, the extraction of chitin requires only one step of hydrolysis of protein.

Once the chitin is extracted, the chitosan is obtained by a deacetylation step, which consists in hydrolyzing acetamide groups. This reaction is generally carried out at high temperature in an alkaline solution, for example a solution of soda (NaOH) at 48% in water, at 90° C.

Due to its crystalline structure, chitin β, which is extracted from endoskeletons of cephalopods, has a better hydrophilia and a greater reactivity to deacetylation. Thus, due, on the one hand, to its crystalline structure, and, on the other hand, to a less aggressive corrosive step during the extraction of chitin β, chitosan β, particularly obtained from endoskeletons of cephalopods, also has a better reactivity and is particularly interesting for medical applications. Chitosan β from chitin β may also attain molecular weights which are impossible to attain with chitosan α from chitin α.

Chitosan β obtained after deacetylation of chitin β has a relatively low acetylation rate, generally in the range of 1 to 10%, giving it a very good solubility in diluted acidic media.

However, according to its desired usage, this chitosan β of low degree of acetylation should for example be reacetylated, that is to say, its degree of acetylation must be increased again, for example to give it specific properties.

Thus, in the field of biodegradable implants which serve as reinforcement for abdominal walls, compounds which give the implant both mechanical properties ensuring the function, even temporary, of reinforcement and support, and a controlled biodegradation, are needed. Thus, according to the kinetics of biodegradation required for the implant, chitosan should have a degree of acetylation of 20, 30, 40, or even 50% or 55%.

Moreover, for such medical and/or pharmaceutical applications, chitosan β must of course be purified and perfectly characterized: in particular, it must have very low rates of bacteria, endotoxins, contaminants, such as heavy metals and insoluble particles; it must not include any risk of viral contamination; its physico-chemical parameters, such as its molecular weight and its polydispersity index must be controlled.

Methods for the purification of chitosan β exist. However, it has been observed that the acetylation of a starting chitosan β having a low degree of acetylation and which is purified was hardly reliable and hardly reproducible from the moment degrees of acetylation higher than or equal to 40% were sought to be attained.

Indeed, the acetylation of a starting chitosan β with a low degree of acetylation, for example ranging from 1 to 10%, is generally carried out by means of acetic anhydride, which is reacted with the quantity of chitosan β sought to be acetylated in stoichiometric proportions, method for which one can be based on a statistical model which allows determining a priori the required quantity of acetic anhydride as follows: the number ($n_{Ch}$-$NH_2$) of amine functions to be acetylated depends on the initial degree of acetylation of the chitosan ($DA_i$) and the degree of acetylation sought to be attained, ($DA_f$). Determining this quantity is hence carried out using the following formula:

$$(n_{Ch}\text{-}NH_2) = (n_{Ch}\text{-}NH_2)_i - (n_{Ch}\text{-}NH_2)_f$$

Where ($n_{Ch}$-$NH_2$)$_i$ is the number of free amine functions of chitosan before acetylation, that is to say, $DA_i$, and ($n_{Ch}$-$NH_2$)$_f$ is the number of free amine functions of chitosan of the degree of acetylation $DA_f$ sought to be attained,
With $$(n_{Ch}\text{-}NH_2)_i = n_{total} \times (1 - DA_i)$$

and $$(n_{Ch}\text{-}NH_2)_f = n_{total} \times (1 - DA_f)$$

$DA_i$ is the initial degree of acetylation of the chitosan β, $DA_f$ is the final degree of acetylation sought to be attained, And $$n_{total} = \frac{m_{chitosan} \times (1 - \% \text{ water})}{M_0}$$

where $-\%_{water}$ represents the moisture content of the initial chitosan β. The considered mass $M_0$ is that of a unit of the polymer of the initial chitosan β.

The mass of acetic anhydride ($m_{aa}$) to be added is obtained by the following relationship:

$$M_{aa} = (n_{Ch}\text{-}NH_2) \times M_{aa}$$

where Maa is the molar mass of the acetic anhydride, in other words 102.09 g·mol$^{-1}$.

Such a method generally allows producing a succession of homogenous lots of reacetylated chitosan with a control of the degradation kinetics of the reacetylated chitosan, the chitosan being reacetylated homogenously.

In order to determine the reproducibility and precision of such a method, for a determined number N of tests, it is measured the value D of the difference between the value of the final desired or theoretical degree of acetylation, namely $DA_L$ and the value of the real or measured degree of acetylation on the end product, in other words the reacetylated chitosan, for example by nuclear magnetic resonance spectroscopy (NMR), namely, $DA_r$. Then the average A of the percentage of differences D is calculated with respect to the theoretical target, and its standard deviation (a) with respect to the number N of carried out tests.

Thus, it has been noted that in the case where the theoretical degree of acetylation was 40% or more for the reacetylation of purified chitosan, the average A and its standard deviation σ, determined as aforementioned, attained too high values, making the method hardly reliable and non reproducible.

Hence, it would be desirable to be able to have a method which allows both purifying and acetylating a chitosan β of low initial degree of acetylation, said method allowing attaining a real degree of acetylation measured on the reacetylated chitosan higher than or equal to 40%, for example close to 50%, said method being reliable and reproducible.

The present invention is about a method for the preparation of chitosan of a degree of acetylation $DA_r$, from chitosan β having a degree of acetylation $DA_i$ lower than $DA_r$, comprising at least one step of purification and at least one step of acetylation of said chitosan β, said purification step comprising at least one step of solubilization of said chitosan β in an acidic aqueous medium and at least one step of precipitation of said thus solubilized chitosan, wherein said acetylation step is carried out in solution on said solubilized chitosan before said precipitation step.

Thus, in the method according to the invention, the purification and the acetylation are carried out in one single global step. The method according to the invention allows obtaining purified chitosans having a high degree of acetylation (DA), for example ranging from 40% to 55%, for example of around 50%, in a reliable and reproducible manner. In particular, in the method of the invention, the absolute value of the average A as mentioned above is for example lower than or equal to 2%, and its standard deviation σ is lower than or equal to 2%.

Thus, thanks to the method according to the invention, it is possible to obtain purified chitosan and having a high DA in a precise manner, and thus, use it in medical and/or pharmaceutical applications. Thus, it is possible to carry out implants having a totally predictable and controlled kinetics of degradation.

In addition, as will become apparent from the following description, the method according to the invention allows getting free from numerous time-consuming washing and drying steps, steps which are generally found in the known methods where the chitosan is purified before being acetylated.

The chitosan β of initial degree of acetylation $DA_i$ constituting the starting material of the method according to the invention may be obtained by deacetylation of the chitin β in the following manner: chitin β, for example extracted from endoskeleton of ground squid, as described above by hydrolyzing proteins, is washed in water then centrifuged. It is then dried.

The thus, ground chitin undergoes a step of deproteinization at room temperature (around 20-25° C.): to do this, chitin in powder form is mixed with a solution of NaOH 1N for 24 h.

The chitin is then washed in successive water baths.

The thus washed chitin is deacetylated in order to obtain chitosan: during this step, the washed chitin is introduced in a bath of NaOH 50% (in weight) at 90° C. for 20 min and then washed. This step is repeated a second time.

The obtained product is dried in an oven: it consists of chitosan of low degree of acetylation.

Chitosan β having a low degree of acetylation is obtained, in other words a degree of acetylation ranging from about 1% to about 10%, for example ranging from 2 to 6%.

The following publications also describe methods for the deacetylation of chitin β in order to obtain chitosan of low degree of acetylation: "Lamarque, G., C. Viton, and A. Domard, *New Route of Deacetylation of α- and β-Chitins by Means of Freeze-Pump Out-Thaw Cycles*. Biomacromolecules, 2005. 6(3):p. 1380-1388.", "Lamarque, G., C. Viton, and A. Domard, *Comparative Study of the First Heterogeneous Deacetylation of α- and β-Chitins in a Multistep Process*. Biomacromolecules, 2004. 5(3):p. 992-1001.", "Lamarque, G., C. Viton, and A. Domard, *Comparative Study of the Second and Third Heterogeneous Deacety-*

*lations of α- and β-Chitins in a Multistep Process.* Biomacromolecules, 2004. 5(5):p. 1899-1907.", "Tolaimate, A., et al., *Contribution to the preparation of chitins and chitosans with controlled physico-chemical properties.* Polymer, 2003. 44(26): p. 7939-7952."

The degree of acetylation of chitosan may be characterized for example by one of the following methods: Fourier transform infrared spectroscopy (FTIR), UV spectrometry, nuclear magnetic resonance (NMR).

In the present application, the degrees of acetylation DAi, DAr and DAf are characterized by Nuclear Magnetic Resonance (NMR) spectroscopy according to the protocol described in the publication of Lavertu M. et al <<A validated $^1$H NMR method for the determination of the degree of deacetylation of chitosan>> Journal of Pharmaceutical and Biomedical Analysis, 32 (2003) 1149-1158.

In a form of implementation of the method according to the invention, $DA_i$ ranges from around 1% to around 10%, for example from 2 to 6%.

The method according to the invention comprises at least one step of purification and at least one step of acetylation of said chitosan β.

The purification step of the method according to the invention comprises a first step of solubilization of the chitosan β in an acidic aqueous medium. For example, the solubilization may be carried out using acetic acid. The chitosan β may for example be solubilized in a solution of demineralized water by adding a stoichiometric quantity of acetic acid. The molar mass of acetic acid is of 60.052 g/mol. The determination of the quantity of acetic acid to be added is carried out by calculating the number of amine functions that are potentially protonable along the chain of chitosan.

The number of amine functions that are potentially protonable is obtained by the following formula:

$$n(NH_2) = \frac{m(chitosan) \times (1 - DA_i) \times (1 - \%_{water})}{M(0)}$$

Wherein $-\%_{water}$ represents the moisture content of starting chitosan and m(chitosan) the dry mass used.

M(0) is the molar mass of chitosan and is calculated based on the following formula:

$$M(0) = 203 \times DA_i + 161 \times (1 - DA_i)$$

Then, the mass of acetic acid (100%) to be added is determined using the following formula:

$$m(CH_3COOH) = n(NH_2) \times M(CH3COOH)$$

where M(CH3COOH) is the molar mass of the acetic acid, namely 60.052 g/mol.

Solubilization is done by stirring until obtaining a homogenous solution. For example, the concentration in chitosan may be set at 0.5% (in weight) in acidic aqueous solution in order to preferably obtain a rather low viscosity in the final solution.

In other implementations of the method according to the invention, solubilization may be carried out using hydrochloric acid, glutamic acid, lactic acid or a mixture thereof.

According to the method of the invention, the step of acetylation of the chitosan is carried out in solution on said solubilized chitosan, before any precipitation step. This allows the chitosan to have very good reactivity with respect to the acetylation.

In a form of implementation of the method according to the invention, a filtration step is carried out after said solubilization step and before said acetylation step, in order to remove the insoluble particles and contaminants that are potentially present in the acidic aqueous solution of chitosan. The filtration of the chitosan solution obtained in the previous step may for example be carried out on porous membranes such as millipore cartridges of porosity 1.0/0.5 µm sold under brand name "Opticap® XL" by the Millipore company.

The solution of chitosan is for example poured into a filtering tank suited to the worked volume and is put under pressure with compressed air, the outlet of the tank being connected to the porous filtering membrane. If necessary, in order to accelerate filtration if necessary, the solution of chitosan may be diluted in demineralized water.

Once the solution is filtered as described above, we proceed to the acetylation step.

The acetylation step comprises for example the addition of acetic anhydride in stoichiometric proportion with respect to the quantity of chitosan to be acetylated in order to obtain said chitosan of degree of acetylation $DA_r$.

The quantity of chitosan to be acetylated, in other words the number ($n_{Ch}$-$NH_2$) of amine functions to be acetylated, depends on the degree of acetylation of the solubilized chitosan (DA) and the degree of acetylation sought to be attained ($DA_f$). Determination of this quantity is hence done using the following formula:

$$(n_{Ch}\text{-}NH_2) = (n_{Ch}\text{-}NH_2)_i - (n_{Ch}\text{-}NH_2)_f$$

Where $(n_{Ch}\text{-}NH_2)_i$ is the number of free amine functions of the solubilized chitosan before acetylation and $(n_{Ch}\text{-}NH_2)_f$ is the number of free amine functions of chitosan of degree of acetylation $DA_f$ sought to be attained, With $$(n_{Ch}\text{-}NH_2)_i = n_{total} \times (1 - DA_i)$$

and $$(n_{Ch}\text{-}NH_2)_f = n_{total} \times (1 - DA_f)$$

$DA_i$ is the initial degree of acetylation of the chitosan, $DA_f$ is the final degree of acetylation sought to be attained, And $$n_{total} = \frac{m_{chitosan} \times (1 - \% \text{ water})}{M_0}$$

The considered mass $M_0$ is that of a unit of the initial chitosan polymer.

The mass of acetic anhydride ($m_{aa}$) to be added is obtained by the following relationship:

$$m_{aa} = (n_{Ch}\text{-}NH_2) \times M_{aa}$$

where Maa is the molar mass of the acetic anhydride, in other words 102.09 g·mol$^{-1}$ Before adding the acetic anhydride to the solubilized chitosan, a co-solvent may be added, for example 1,2-Propanediol to the solution of chitosan. The addition of such a co-solvent allows homogenizing the reaction.

Then, the acetic anhydride is added in stoichiometric proportion, as determined above. The set is preferably mixed under stirring.

Once the acetylation step carried out, the purification of the chitosan is continued with a precipitation step in order to obtain a precipitate of chitosan.

In a form of implementation of the method according to the invention, the precipitation step comprises adjusting at a pH ranging from 9.5 to 11 the chitosan obtained after the acetylation step.

The precipitation step may include a viral deactivation step. The viral deactivation step is a step which allows hydrolyzing the components related to the viruses, prions and residual toxins.

Thus, in a form of implementation of the method according to the invention, the step of precipitation comprises:

A first precipitation at a pH ranging from 9.5 to 12 of the chitosan obtained after the acetylation step, A viral deactivation step with a molar concentration of NaOH strictly higher than 1N of the precipitate of chitosan obtained at the end of said first precipitation, A second precipitation at a pH ranging from 9.5 to 11 of the chitosan obtained after said viral deactivation step.

For example, in a mode of implementation of the method according to the invention, a first precipitation of the chitosan obtained after the acetylation step is carried out in basic medium. For example, a solution of soda 5N is prepared. Before the precipitation, the solution of reacetylated chitosan, in other words obtained after the acetylation step, is preferably filtered. The solution is then taken to a pH ranging from 9.5 to 12 to carry out the precipitation. The precipitate of chitosan is recovered by filtration.

In a form of implementation of the method according to the invention, a viral deactivation step is carried out on the precipitate at the end of this first precipitation. For example, to this end, the precipitate recovered by filtration is plunged under mechanical stirring in a quantity of soda which allows attaining a molar concentration of NaOH higher than 1N, for example a pH higher than or equal to 12. For example, the viral deactivation step comprises a solubilization of the precipitate of chitosan obtained at the end of said first precipitation in a solution of sodium hydroxide. The increase of the degree of acetylation of the chitosan with respect to its initial degree of acetylation promotes the solubilization of the chitosan during this viral deactivation step. Thus, at the end of the viral deactivation step, the reacetylated chitosan may again be in solubilized form.

In a form of implementation of the method of the invention, a second precipitation is then carried out, this time on the solution of reacetylated chitosan obtained at the end of the viral deactivation step. The solution of chitosan being highly basic, for example with a molar concentration of NaOH higher than 1N after the viral deactivation step, the precipitation may be carried out by means of addition of glacial acetic acid until obtaining a pH ranging from 9.5 to 11. The obtained precipitate of chitosan is recovered, which is the purified chitosan. This chitosan thus has a degree of acetylation $DA_r$.

In a form of implementation of the method of the invention, a washing step is carried out on the precipitate of chitosan obtained at the end of the precipitation step, in other words on the precipitate obtained from the second precipitation when the precipitation step includes a viral deactivation step as described above. This washing step may for example be carried out with sterile water up to a neutral pH, then for example with ethanol until obtaining a conductivity lower than 1 µS/cm.

In a form of implementation of the method of the invention, the washed precipitate of purified chitosan of degree of acetylation $DA_r$ is dried, for example under laminar flow.

The invention and its advantages will become more apparent with the examples below.

EXAMPLE 1

According to the Invention

It is provided chitosan β obtained as follows: grinding of squid pen, then deproteinization of the powder of squid pen in soda 1N, and extensive deacetylation in a solution of soda 48% (in weight) in order to obtain a chitosan β of initial degree of acetylation $DA_i$ of around 3%. The molar mass of chitosan is of 162.26 g/mol.

In the present example, the degrees of acetylation $DA_i$ and $DA_r$ are characterized by the Nuclear Magnetic Resonance spectroscopy (NMR) according to the protocol described in the publication of Lavertu M. et al <<A validated $^1$H NMR method for the determination of the degree of deacetylation of chitosan>> Journal of Pharmaceutical and Biomedical Analysis, 32 (2003) 1149-1158.

We proceeded to the purification and the acetylation of chitosan β as follows:

In a first step, 55.38 g of chitosan were solubilized in 5 liters of demineralized water to which were added acetic acid in stoichiometric quantity, namely 18.88 ml of acetic acid. The solubilization is carried out under stirring at a temperature of around 50° C. for around 2 h40, until obtaining a homogenous solution.

The solution is then filtered on a millipore cartridge of porosity 1.0/0.5 µm sold under brand name "Opticap® XL" by the Millipore company.

Then 400 ml of 1,2-Propanediol were added to the solution of chitosan.

The quantity of acetic anhydride to be added, namely the stoichiometric quantity, has been determined using the following formulae for a desired final degree of acetylation $DA_f$ of around 50%:

$$(n_{Ch}\text{-}NH_2) = (n_{Ch}\text{-}NH_2)_i - (n_{Ch}\text{-}NH_2)_f$$

Where $(n_{Ch}\text{-}NH_2)_i$ is the number of free amine functions of the solubilized chitosan before acetylation and $(n_{Ch}\text{-}NH_2)_f$ is the number of free amine functions of the chitosan of degree of acetylation $DA_f$ desired to be attained, With $$(n_{Ch}\text{-}NH_2)_i = n_{total} \times (1-DA_i)$$

and $$(n_{Ch}\text{-}NH_2)_f = n_{total} \times (1-DA_f)$$

$DA_i$ is the initial degree of acetylation of the chitosan, $DA_f$ is the final degree of acetylation desired to be attained, And $$n_{total} = \frac{m_{chitosan} \times (1 - \% \text{ water})}{M_0}$$

The considered mass $M_0$ is that of a unit of the polymer of initial chitosan.

The mass of acetic anhydride ($m_{aa}$) to be added is obtained by the following relationship:

$$m_{aa} = (n_{Ch}\text{-}NH_2) \times M_{aa}$$

where Maa is the molar mass of the acetic anhydride, in other words 102.09 g·mol$^{-1}$ 14.791 g of acetic anhydride were added to proceed to the acetylation.

Then the purification of chitosan was carried out using a solution of soda 5N. 100 ml of soda is poured to take the solution of chitosan to a pH of 11.56.

A viral deactivation step is carried out on the precipitate obtained at the end of this first precipitation. To this end, the precipitate recovered by filtration is plunged by mechanical stirring in a quantity of soda which allows attaining a molar concentration of NaOH strictly higher than 1N, for example here a pH of around 12.66, for around 1 hour.

The solution is precipitated again by adding acetic acid until obtaining a pH of around 9.53.

The obtained precipitate is then washed with sterile water until obtaining a washing water with neutral pH, then with ethanol until obtaining a conductivity for the washing water lower than 1 µS/cm. The precipitate of purified chitosan is dried in a vacuum oven for around 96 h. 41.6 g of dry reacetylated and purified chitosan is recovered.

We proceeded to nineteen tests.

For each test, the real degree of acetylation $DA_r$ obtained has been measured by Nuclear Magnetic Resonance spectroscopy according to the aforementioned method.

For each test, the value D was then determined from the difference between the value of the final desired or theoretical degree of acetylation, namely $DA_f$, and the value of the real or measured degree of acetylation on the end product, in other words the reacetylated chitosan, for example by nuclear magnetic resonance (NMR), namely $DA_r$.

Values $DA_f$, $DA_r$ and D are gathered in the following table I:

TABLE I differences between values of theoretical DA ($DA_f$) and measured DA ($DA_r$)

| Tests | DAf | DAr | D = DAf − DAr |
|---|---|---|---|
| 1 | 46.18% | 44.00% | 2.18% |
| 2 | 50.05% | 49.00% | 1.05% |
| 3 | 50.04% | 49.00% | 1.04% |
| 4 | 50.12% | 50.00% | 0.12% |
| 5 | 50.04% | 48.00% | 2.04% |
| 6 | 50.02% | 50.00% | 0.02% |
| 7 | 49.96% | 48.00% | 1.96% |
| 8 | 50.03% | 51.00% | −0.97% |
| 9 | 50.02% | 49.00% | 1.02% |
| 10 | 52.92% | 51.00% | 1.92% |
| 11 | 49.66% | 45.00% | 4.66% |
| 12 | 50.00% | 50.00% | 0.00% |
| 13 | 50.00% | 50.00% | 0.00% |
| 14 | 50.00% | 48.00% | 2.00% |
| 15 | 50.39% | 49.00% | 1.39% |
| 16 | 50.38% | 43.00% | 7.38% |
| 17 | 50.37% | 49.00% | 1.37% |
| 18 | 50.37% | 49.00% | 1.37% |
| 19 | 50.37% | 49.00% | 1.37% |
| Average | 50.05% | 48.47% | 1.57% |
| Standard deviation | 1.15% | 2.20% | 1.84% |

The average of the differences D is calculated on the set of the 19 carried out tests. Statistical analyses are carried out with the "Minitab® 16.2" software of Microsoft. Thus, the average of the differences is equal to 1.57%±1.84%.

Thus, the reproducibility and precision of the method according to the invention is excellent and allows obtaining chitosan having a degree of acetylation higher than 40%, for example here approximately equal to 50%, in a very reliable, reproducible and precise manner.

EXAMPLE 2

Comparative

It is provided the same chitosan β as in Example 1, obtained in the same manner and with the same degree of acetylation $DA_i$ of 3%.

The added quantities of acetic anhydride have been determined using the same formula as in Example 1 for each final desired degree of acetylation $DA_f$, namely around 50%.

However, the purification and the acetylation of the chitosan β were carried out in two separate steps, the purification in a first step, then the acetylation in a second step.

1°) Purification:

In a first step, 110.4 g of chitosan were solubilized in 20 liters of demineralized water to which were added the acetic acid in stoichiometric quantity, namely 40 ml of acetic acid.

The solution is then filtered on a millipore cartridge of porosity 1.0/0.5 µm sold under brand name "Opticap® XL" by the Millipore company.

Then, we proceeded to the purification of the chitosan using a solution of soda 5N. 150 ml of soda is poured to take the solution of chitosan to a pH of 11.79.

A viral deactivation step is carried out on the precipitate from this first precipitation. To this end, the precipitate recovered by filtration is plunged by mechanical stirring in a quantity of soda which allows reaching a molar concentration of NaOH of 2N.

The obtained precipitate is then washed with sterile water until obtaining a washing water with neutral pH, then with ethanol until obtaining a conductivity for the washing water lower than 1 µS/cm.

2°) Reacetylation:

34.2 g of chitosan obtained in step 1°) are solubilized in 3 liters of demineralized water to which were added acetic acid in stoichiometric quantity, namely 10.9 g.

Then, 2500 ml of 1,2-Propanediol is added to the solution of chitosan.

9.1 g of acetic anhydride is added to proceed to the acetylation.

The solution was then precipitated using a solution of soda 5N. 71.6 ml of soda is poured to take the solution of chitosan to a pH of 11.6.

The obtained precipitate is then washed with sterile water until obtaining a washing water with neutral pH, then with ethanol until obtaining a conductivity for the washing water lower than 1 µS/cm. The purified precipitate of chitosan is dried by lyophilization. 35.5 g of dry reacetylated and purified chitosan is recovered.

We proceeded to 58 tests.

For each test, the real degree of acetylation obtained $DA_r$ has been measured by Nuclear Magnetic Resonance according to the protocol described in Example 1.

For each test, we then determined the value D of the difference between the value of the final desired or theoretical degree of acetylation, namely $DA_f$, and the value of the real or measured degree of acetylation on the end product, in other words the reacetylated chitosan, for example by nuclear magnetic resonance (NMR), namely $DA_r$.

We then calculated the average of the differences D on the set of 58 carried out tests. The statistical analyses are carried out with the "Minitab® 16.1" software of Microsoft. Thus, the average of the differences D is equal to −2.65%±2.84%.

Thus, the average of the differences D is high and does not allow carrying out the purification and the acetylation of the chitosan β in a reliable, precise and reproducible manner.

The invention claimed is:

1. A method for the preparation of chitosan of a degree of acetylation $DA_r$, from chitosan β having a degree of acetylation $DA_i$ lower than $DA_r$, comprising at least one step of purification and at least one step of acetylation of said chitosan β, said purification step comprising at least one step of solubilization of said chitosan β in an acidic aqueous medium and at least one step of precipitation of said thus solubilized chitosan, said acetylation step being carried out in a solution on said solubilized chitosan before said precipitation step, wherein the precipitation step includes a viral deactivation step.

2. The method according to claim 1, wherein $DA_i$ ranges from about 1% to about 10%.

3. The method according to claim 1, wherein a filtration step is carried out after said solubilization step and before said acetylation step, in order to remove the insoluble particles and contaminants that are potentially present in the acidic aqueous solution of chitosan.

4. The method according claim 1, wherein the precipitation step comprises adjusting at a pH ranging from 9.5 to 11 the chitosan obtained after the acetylation step.

5. The method according to claim 1, wherein the precipitation step comprises:
   a first precipitation at a pH ranging from 9.5 to 12 of the chitosan obtained after the acetylation step,
   a viral deactivation step with a molar concentration of NaOH higher than 1N of the precipitate of chitosan obtained at the end of said first precipitation which forms a chitosan solution,
   a second precipitation at a pH ranging from 9.5 to 11 of the chitosan obtained at the end of said viral deactivation step.

6. The method according to claim 4, wherein the precipitation step comprises:
   a first precipitation at a pH ranging from 9.5 to 12 of the chitosan obtained after the acetylation step,
   a viral deactivation step with a molar concentration of NaOH higher than 1N of the precipitate of chitosan obtained at the end of said first precipitation which forms a chitosan solution,
   a second precipitation at a pH ranging from 9.5 to 11 of the chitosan obtained at the end of said viral deactivation step.

7. The method according to claim 1, wherein a washing step is carried out on the precipitate of chitosan obtained at the end of said precipitation step.

8. The method according to claim 5, wherein a washing step is carried out on the precipitate of chitosan obtained at the end of said precipitation step.

9. The method according to claim 6, wherein a washing step is carried out on the precipitate of chitosan obtained at the end of said precipitation step.

10. The method according to claim 1, wherein the solubilization in acidic aqueous medium is carried out using acetic acid.

11. The method according to claim 1, wherein the acetylation step comprises the addition of acetic anhydride in stoichiometric proportion with respect to the quantity of chitosan β to be acetylated in order to obtain said chitosan of degree of acetylation $DA_f$.

12. The method according to claim 1, wherein the viral deactivation step comprises a solubilization of a precipitate of chitosan obtained at the end of a first precipitation in a solution of sodium hydroxide.

13. The method according to claim 5, wherein the viral deactivation step comprises a solubilization of the precipitate of chitosan obtained at the end of said first precipitation in a solution of sodium hydroxide.

14. The method according to claim 6, wherein the viral deactivation step comprises a solubilization of the precipitate of chitosan obtained at the end of said first precipitation in a solution of sodium hydroxide.

15. The method according to claim 1, wherein $DA_i$ ranges from 2 to 6%.

16. The method according to claim 5, wherein the solubilization in acidic aqueous medium is carried out using acetic acid.

17. The method according to claim 6, wherein the solubilization in acidic aqueous medium is carried out using acetic acid.

18. The method according to claim 5, wherein the acetylation step comprises the addition of acetic anhydride in stoichiometric proportion with respect to the quantity of chitosan β to be acetylated in order to obtain said chitosan of degree of acetylation $DA_f$.

19. The method according to claim 6, wherein the acetylation step comprises the addition of acetic anhydride in stoichiometric proportion with respect to the quantity of chitosan β to be acetylated in order to obtain said chitosan of degree of acetylation $DA_f$.

* * * * *